(12) United States Patent
Alam et al.

(10) Patent No.: US 10,067,065 B1
(45) Date of Patent: Sep. 4, 2018

(54) ELECTRONIC DEVICE INSPECTING SYSTEM AND METHOD

(71) Applicant: Amazon Technologies, Inc., Reno, NV (US)

(72) Inventors: Mohammed Aftab Alam, San Jose, CA (US); Vikram Srinivas, San Jose, CA (US); Nageswara Rao Tadepalli, Sunnyvale, CA (US); Bobak Ranjbaran, Sunnyvale, CA (US); Ramez Nachman, San Francisco, CA (US)

(73) Assignee: AMAZON TECHNOLOGIES, INC., Reno, NV (US)

(*) Notice: Subject to any disclaimer, the term of this patent is extended or adjusted under 35 U.S.C. 154(b) by 793 days.

(21) Appl. No.: 14/311,585

(22) Filed: Jun. 23, 2014

(51) Int. Cl.
*G01N 21/88* (2006.01)

(52) U.S. Cl.
CPC .............................. *G01N 21/8803* (2013.01)

(58) Field of Classification Search
CPC ............ G01N 21/8806; G01N 21/8851; G06T 7/0004
See application file for complete search history.

(56) References Cited

U.S. PATENT DOCUMENTS

| | | | |
|---|---|---|---|
| 5,621,218 A * | 4/1997 | Tanaka | G01N 21/95684 250/559.22 |
| 6,766,046 B1 | 7/2004 | Saito et al. | |
| 7,330,250 B2 | 2/2008 | Gip et al. | |
| 8,676,045 B1 | 3/2014 | Sawatzky et al. | |
| 2009/0087079 A1* | 4/2009 | Onoda | G06K 9/00 382/141 |
| 2010/0245560 A1 | 9/2010 | Aldred | |
| 2012/0019736 A1* | 1/2012 | Yamamoto | G03B 35/02 349/15 |
| 2012/0051514 A1* | 3/2012 | Sims | A61B 5/0035 378/63 |
| 2014/0146165 A1* | 5/2014 | Furnas | G01N 21/896 348/92 |

* cited by examiner

*Primary Examiner* — Md Haque
*Assistant Examiner* — Berteau Joisil
(74) *Attorney, Agent, or Firm* — K&L Gates LLP (57) ABSTRACT

A cover glass of an electronic device may be inspected for defects and damage such as cracks, fractures, scratches, and chips. The electronic device may be placed in an enclosure with a lighting assembly that emits light to the electronic device, and scattered light from defects and damage of the cover glass is captured by an imaging device. A shutter assembly facilitates the capture of scattered light and reduces the capture of reflected light, which enhances the exposure of defects and damage of the captured image of the cover glass. A mirror facilitates the capture of a side surface of the electronic device.

19 Claims, 9 Drawing Sheets

ELECTRONIC DEVICE INSPECTING SYSTEM AND METHOD

BACKGROUND

Many electronic devices, such as tablet computers, electronic book readers, smartphones, and other mobile computing devices, include a protective cover glass through which a graphical display may be viewed. Although the cover glass may be toughened to resist cracks, fractures, fragmentations, scratches, chips, and the like, the cover glass may still be subject to manufacturing defects as well as damage from various stages of the life cycle of the cover glass, such as assembly with and usage of an electronic device. Under certain circumstances, such as quality assurance testing, it is desirable to be able to test for damage, flaws or defects of the cover glass after assembly of an electronic device. Additionally, it is desirable to be able to document damage after an electronic device has been used. For example, if a user returns a damaged device, it may be desirable for a return center to be able to document flaws or defects of returned electronic devices.

Accordingly, there is a need to improve the inspection process for an electronic device.

DETAILED DESCRIPTION

In the following description, reference is made to the accompanying drawings which illustrate several embodiments of the present disclosure. It is to be understood that other embodiments may be utilized and system or process changes may be made without departing from the spirit and scope of the present disclosure. The following detailed description is not to be taken in a limiting sense, and the scope of the embodiments of the present invention is defined only by the claims of the issued patent. It is to be understood that drawings are not necessarily drawn to scale.

In accordance with embodiments of the present invention, an object, such as an electronic device, may be inspected. For example, a cover glass of the electronic device may be inspected for defects and damage such as cracks, fractures, fragmentations, scratches, chips, and the like. It is to be understood that an embodiment may include any object that includes glass, tempered glass, laminated glass, or a glass equivalent on a portion of an exterior surface. The object may be placed in an enclosure with a lighting assembly that emits or directs light toward the object, and scattered light from defects of the object may be captured by an imaging device. A shutter assembly may allow, permit or facilitate the capture of scattered light and may restrict or reduce the capture of reflected light, which may enhance the exposure or visibility of defects of the captured image of the object.

Figure 1:
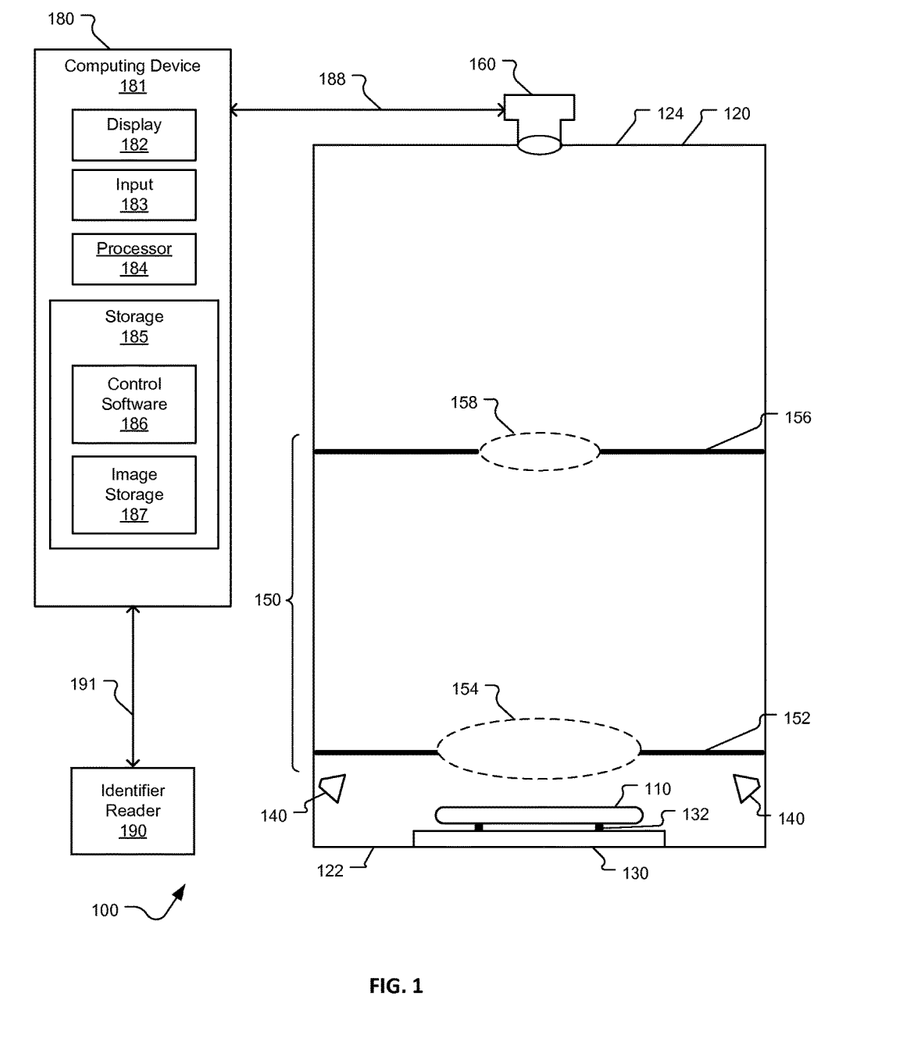
FIG. 1 is a block diagram illustrating an inspection system, in accordance with embodiments of the present invention.

FIG. 1 is a block diagram illustrating an inspection system 100, in accordance with embodiments of the present invention. An object 110, such as an electronic device, may be placed in an enclosure 120, such as a box, a photographic booth, a room, a building, or the like. The enclosure 120 may be formed from a variety of opaque materials, such as, e.g., acrylic sheets, plywood, cardboard, and the like. An imaging device 160, such as a camera, may capture an image of the object 110. The enclosure may enclose the object 110 within the walls of the enclosure 120. The enclosure may have an interior surface that reduces the reflection of light, such as a matte surface, a black colored surface, a black matte finished surface, a light diffusing surface, a light absorbing surface, or the like.

Under an embodiment, the enclosure 120 has a box shape, and the object 110, such as an electronic device, may be placed at a first end 122 of the enclosure 120. For example, the object 110 may be placed with a surface of the object 110 resting on an inner surface of the enclosure 120 closest to the ground, for example the bottom of the enclosure 120. In this embodiment, gravity may keep the object 110 in place. In other embodiments, a support fixture 130 may be utilized to counteract gravity causing the object 110 to not remain in a desired position. It is to be understood that the object 110 may have a shape that causes it to move, roll or fall. For example, it may be desirable to place an electronic device on its edge, and the support fixture 130 can support the electronic device from falling over. It is to be further understood that it may be desirable to place the object 110 on an inner surface of the enclosure 120 that is not closest to the ground. For example, the first end 122 of the enclosure 120 may be a side wall, and the support fixture 130 may allow the electronic device to be supported or coupled to such a side wall. Under some embodiments, the object 110 may be placed on or coupled to the support fixture 130 at the first end 122 of the enclosure 120. In order to improve the support of the support fixture 130, the support fixture 130 may comprise at least one support component 132, such as a fastener or a platform, to support the object 110.

The support fixture 130 may have a form that is specific to the object 110 being inspected. For example, the support fixture 130 may be sized to receive a 7 inch tablet electronic device or a 9 inch tablet electronic device. The support fixture 130 may be removable from the enclosure 120, such that the enclosure can accommodate different objects 110. Furthermore, with a removable support fixture 130, the object 110 may be coupled to the support fixture 130 before the support fixture 130 is placed into the enclosure 120. A support fixture 130 may be three-dimensional printed, additive manufactured, or machined. The support fixture 130 may comprise an acrylonitrile butadiene styrene (ABS) material, or the like.

The enclosure 120 may include a lighting assembly 140 comprising one or more light sources. The light source may be polymeric light such as a light-emitting diode (LED), incandescence light, halogen light, fluorescent light, high intensity discharge light, laser light, or the like. The light emitted from the light source may be generally collimated or generally diffused. The light source of the lighting assembly 140 may emit or direct light at an angle of incidence in relation to the object's 110 surface, such as a cover glass. As discussed further below, light may generally be reflected by the object 110, and light may be scattered by the object's 110 defects or flaws, such as a crack in the cover glass. A defect or flaw may be structural, cosmetic, or the like. In some embodiments, visible defects or flaws of the object 110 that are visible to a typical human eye may be captured in an image.

Under some embodiments, the lighting assembly 140 may surround the object 110 or the support fixture 130. For example, the light source may be coupled to each wall of the enclosure 120. The lighting assembly 140 may also generally take the shape of the object 110. For example, if the object 110 is a rectangular tablet electronic device, then the lighting assembly 140 that surrounds the rectangular object 110 may also be rectangular. Alternatively, if the object 110 is circular, then the lighting assembly 140 that surrounds the circular object 110 may also be circular. Under some embodiments, the lighting assembly 140 may comprise a group of LEDs along each wall of the enclosure 120. For example, if the enclosure 120 has four walls, then there may be four groups of LEDs, with each group coupled to a respective one of the four walls of the enclosure. Under some embodiments, a group of LEDs may comprise an array or plurality of LEDs. It is to be understood that under some embodiments, the lighting assembly 140 may comprise light sources that are coupled to fewer than all the walls of the enclosure 120.

The enclosure 120 may include a shutter assembly 150 that may comprise one or more shutters. As shown in FIG. 1, the shutter assembly 150 may comprise a first shutter 152 having a first opening 154 and a second shutter 156 having a second opening 158. The shutter of the shutter assembly 150 may be a sheet or a plate with an opening, aperture, or hole. The shutter may comprise an opaque material such as cardboard, metal, plastic, or the like. Under some embodiments, the shutter may have a surface that reduces the reflection of light, such as a matte surface, a black colored surface, a black matte finished surface, a light diffusing surface, a light absorbing surface, or the like. For example, a sheet of cardboard may be cut to have a dimension of an interior cross section of the enclosure 120, and an opening, aperture, or hole may be cut in the approximate center of the cardboard to form the opening. The sheet or plate of the shutter may block light from passing from one side of the shutter to the opposing side, such as providing a hard stop of light, while the opening, aperture or hole of the shutter may allow light to pass from one side of the shutter to the opposing side.

In some embodiments, as shown in FIG. 1, the first shutter 152 may be positioned between the lighting assembly 140 and an opposing second end 124 of the enclosure 120, and the second shutter 156 may be positioned between the first shutter 152 and the second end 124 of the enclosure 120. In some embodiments, the first shutter 152 may be positioned proximate to the lighting assembly 140. It is to be understood that any number of shutters may be included with the shutter assembly 150. For example, although not shown, the enclosure 120 illustrated in FIG. 1 may include a third shutter having a third opening, and such a third shutter may be located between the first shutter 152 and the second shutter 156 or between the second shutter 156 and the second end 124 of the enclosure 120.

The size of the opening of the shutter may be based on the focal length of a lens of the imaging device 160 as well as on the size of the object 110. For example, the opening may have a size so that the imaging device 160 may capture via the lens an image of a complete object 110, such as the object's 110 surface area facing the imaging device 160. In addition, the opening may have a size so that the imaging device 160 does not capture an image of a substantial portion of the area surrounding the object 110. It is to be understood that because the first opening 154 of the first shutter 152 is further away from the imaging device 160 than the second opening 158 of the second shutter 156, the first opening 104 may be sized larger than the second opening 158 in order for the imaging device 160 to capture a complete image of the object 110. Furthermore, the dimension of the opening of the shutter may be based on the dimension of the object 110. For example, if the object 110 is rectangular shaped, then the opening of the shutter may also be rectangular shaped.

The imaging device 160, such as a camera, may be coupled to the second end 124 of the enclosure 120. The imaging device 160 may be a point and shoot camera, a single lens reflex camera, or the like. The imaging device 160 may have a fixed focal length lens or a variable focal length lens, which may allow zooming into a particular area of the object 110. An example of the imaging device 160 may be a Nikon D5100 with a 50 millimeter fixed focal length lens. The imaging device 160 may be coupled to the interior of the enclosure 120, or may be coupled to the exterior of the enclosure 120 with the lens positioned in an aperture of the enclosure 120. Under some embodiments, a polarizing filter may be coupled to the lens of the imaging device 160. Such a polarizing filter may filter or cancel light reflected off of the interior surfaces of the enclosure 120. For example, light may be reflected from the object 110 and may subsequently be reflected from the interior surface of the enclosure, becoming polarized or partially polarized light. Such polarized light may pass through the openings of the shutters and a filter may filter or block the polarized light from being received by the imaging device 160. The imaging device 160 may comprise a body, a lens, a sensor comprising light sensitive pixels, a processor, and a memory. The sensor may receive light via the lens, measure the intensity of the light, and generate or determine image data such as light intensity values and the position of the associated pixel. The generated image data may be stored in the memory and may be used to construct an image.

It is to be understood that under some embodiments of the inspection system 100, the light sources of the lighting assembly 140 can be programmed to generally emit light continuously, and each opening of the shutter assembly 150 is continuously open with a fixed position. In alternative embodiments, a shutter of the shutter assembly 150 may be configured and programmed to open and close and the lighting assembly 140 may emit a flash of light, such that the opening of the shutter assembly 150 and/or the flash of the lighting assembly 140 may be synchronized with the capturing of an image with the imaging device 160. In another alternative embodiment, the lighting assembly 140 may comprise a laser that may scan the surface of the object 110 in synchronization with the capturing of an image by the imaging device 160.

The inspection system 100 may include a control system 180 comprising a computing device 181 coupled to the imaging device 160 via a control channel 188. The control system 180 may also be coupled to a reader 190 via a reader channel 191. The control system 180 may control the operations of the imaging device 160, such as capturing an image of the object 110 placed within the enclosure 120. Furthermore, the control system 180 may store the image captured by the imaging device 160. The reader 190 may be controlled to scan, read or otherwise detect an identifier of the object 110, such as a data source name (DSN), via a barcode, a quick response (QR) code, a radio-frequency identification (RFID) tag or chip, or the like. The reader 190 may be a barcode scanner, a QR code reader, an RFID reader, a real-time locating system (RTLS), or the like. The control system 180 may store or associate the identifier corresponding to the object 110 being inspected with the corresponding image that was captured by the imaging device 160. For example, the image file name may be the identifier. The image file may also be communicated, sent or delivered to a third party for further analysis.

The computing device 181 may be implemented as any of a number of computing devices, such as a tablet computing device, a laptop computer, a desktop computer, a server computer, and other devices providing control functionality. It should be understood that various types of computing devices that include a processing element, a memory, and a user interface can be used in accordance with various embodiments discussed herein. It should also be understood that the control channel 188 or the reader channel 191 may be wired or wireless. For example, an imaging device 160 may be controlled by the computing device 181 with a wireless protocol such as Bluetooth, cellular, IEEE 802.11, or infrared communications protocols, such as an IrDA-compliant protocol.

The computing device 181 may include a display screen 182 or display component. The display screen 182 may comprise, for example, one or more devices such as cathode ray tubes (CRTs), liquid crystal display (LCD) screens, gas plasma-based flat panel displays, LCD projectors, LED displays, electronic paper displays, electrowetting displays, or other types of display devices and display screens, etc. The computing device 181 may also include one or more input devices 183 operable to receive inputs from a user. The input devices 183 can include, for example, a push button, touch pad, touch screen, wheel, joystick, keyboard, mouse, trackball, keypad, accelerometer, light gun, game controller, or any other such device or element whereby a user can provide inputs to the computing device 181. These input devices 183 may be incorporated into the computing device 181 or operably coupled to the computing device 181 via wired or wireless interfaces. For computing devices with touch sensitive displays, the input devices 183 can include a touch sensor that operates in conjunction with the display screen 182 to permit users to interact with the image displayed by the display screen 182 using touch inputs (e.g., with a finger or stylus).

The computing device 181 may also include a processing element 184 for executing instructions and retrieving data stored in a storage element 185. As would be apparent to one of ordinary skill in the art, the storage element 185 can include one or more different types of memory, data storage or computer-readable storage media, such as, for example, a control software storage 186 for control software execution or program instructions for execution by the processing element 184, and an image data storage 187 for images or data.

Figure 2:
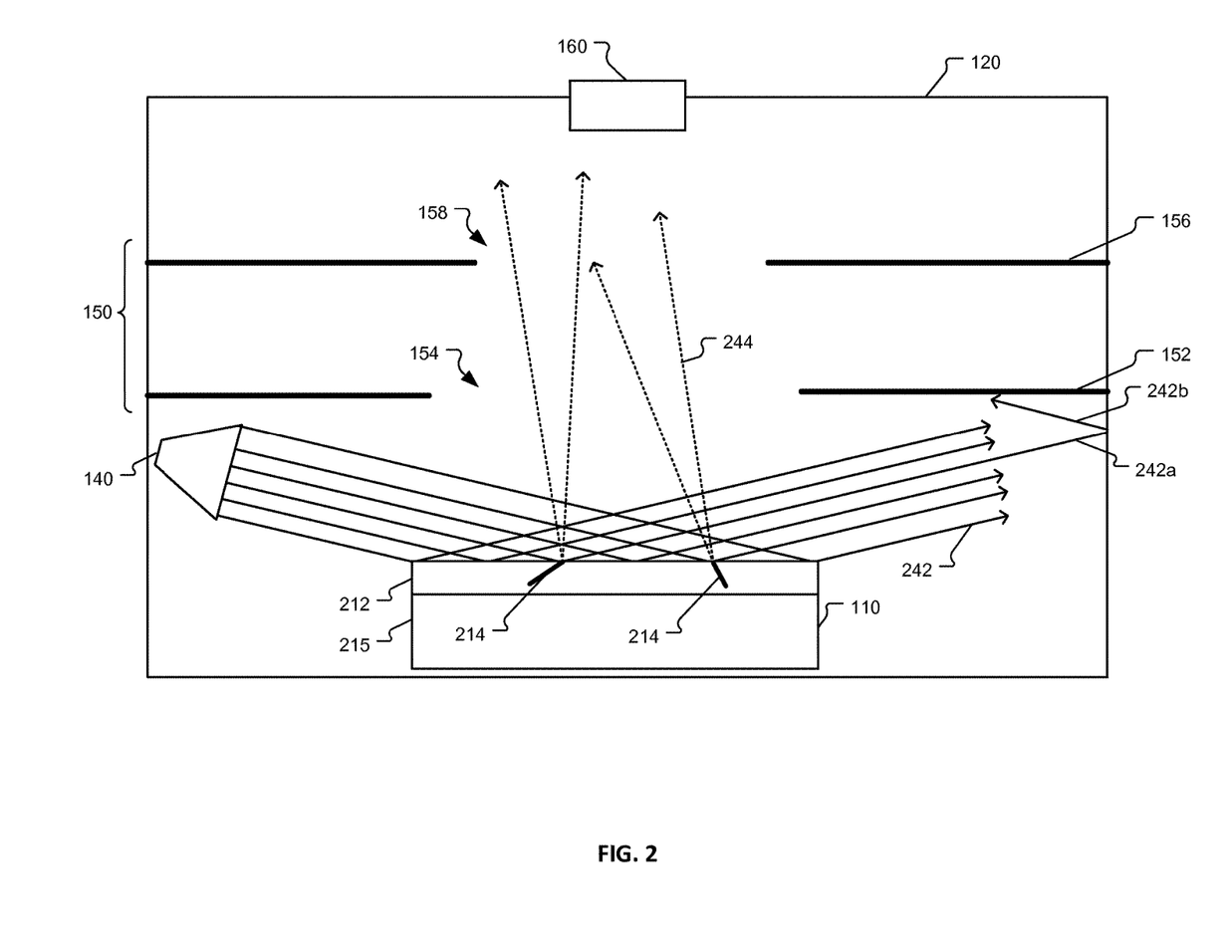
FIG. 2 is a block diagram illustrating a schematic cross-sectional view of an enclosure, in accordance with embodiments of the present invention.

FIG. 2 is a block diagram illustrating a schematic cross-sectional view of an enclosure 120, in accordance with embodiments of the present invention. As shown in FIG. 2, the lighting assembly 140 may emit light directed toward the object 110. The object 110 may comprise the cover glass 212 or other light reflectable surface, which may be coupled to an opaque component 215, such as the housing of an electronic device or a substrate. The opaque component 215 may prevent light from passing through the object 110, such as when light is directed at the cover glass 212. Under some embodiments, the cover glass 212 may have at least one crack 214 or other light scattering feature. As illustrated, light from the lighting assembly 140 may be emitted toward the cover glass 212 of the object 110, which may become reflected light 242 or scattered light 244. Reflected light 242 may be reflected by the cover glass 212 and may be partially blocked from passing past the first shutter 152 or the second shutter 156. For example, primary reflected light 242a may be reflected by the object 110, and secondary reflected light 242b may be reflected by the internal surface of the enclosure 120, and, as illustrated in FIG. 2, the secondary reflected light 242b may be blocked from passing past the shutter 152. It is to be understood that secondary reflected light 242b may be reflected by any component of the enclosure 120, such as a wall, a shutter, and the like. Scattered light 244 may be scattered by the crack 214, and may pass through the first opening 154 of the first shutter 152 and through the second opening 158 of the second shutter 156 to the imaging device 160. In some embodiments, the shutter assembly 150 may block substantially all of the reflected light 242, and in other embodiments, the shutter assembly may block a portion of the reflected light 242. In some embodiments, the shutter assembly 150 may reduce the optical noise of the reflected light 242.

The lighting assembly 140 may comprise one or more light sources, which may emit generally, approximately, or substantially collimated light. For example, as illustrated in FIG. 2, light emitted from the light source of the lighting assembly 140 is illustrated with substantially parallel rays of light. Under some embodiments, the light source may be an LED, a laser, or the like. Under some embodiments, the light source may be collimated with a collimator such as a collimating mirror, a collimating lens, or the like. For example, an LED may be placed at the focus of a parabolic mirror or a parabolic reflector, which may align the emitted light from the LED in a specific direction or cause the emitted light to be reflected outward in a beam approximately focused at infinity.

Under some embodiments, light may be emitted toward the object 110 at an angle of incidence with respect to the normal of the cover glass 212. The angle of incidence in some embodiments may be greater than about 0 degrees and less than about 90 degrees. In some embodiments, oblique lighting or side lighting may be utilized. For example, as depicted in FIG. 1, the angle of incidence may be grazing, glancing, greater than about 45 degrees and less than about 90 degrees, or may be greater than about 70 degrees and less than about 80 degrees. Such lighting may highlight features that cause light to be scattered in multiple directions, such as the crack 214. It is to be understood that the scattering of light will depend on many factors, such as the type of crack 214, the orientation of the crack 214, the placement of each of the light sources of the lighting assembly 140 around the object 110, and the angle of incidence of each of the light sources of the lighting assembly 140.

Under some embodiments, to improve the scattering of light by the crack 214, the lighting assembly 140 may comprise one or more radially symmetric light sources that shine light from all sides of the object 110 such that light rays are received by the object 110 from substantially 360 degrees.

Under some embodiments, the lighting assembly 140 may comprise groups of light sources positioned at different angles of incidence to the object 110. For example, a plurality of images of the object 110 may be captured when each respective group of light sources emits light at the respective angle of incidence. Such may increase the probability of capturing an image of cracks 214. Under some embodiments the plurality of images may be combined or merged into a single image using image processing software, such as the Image Processing Toolbox from MathWorks, Inc. Such merging of the images may achieve increased resolution of the crack 214.

Under some embodiments, the control system 180 or other computing device may perform various image processing analyses of the crack 214 or other visible feature captured in an image of the cover glass 212. For example, a crack may be characterized, a crack may be distinguished from another crack, a crack may be automatically detected, and the like.

Figure 3:
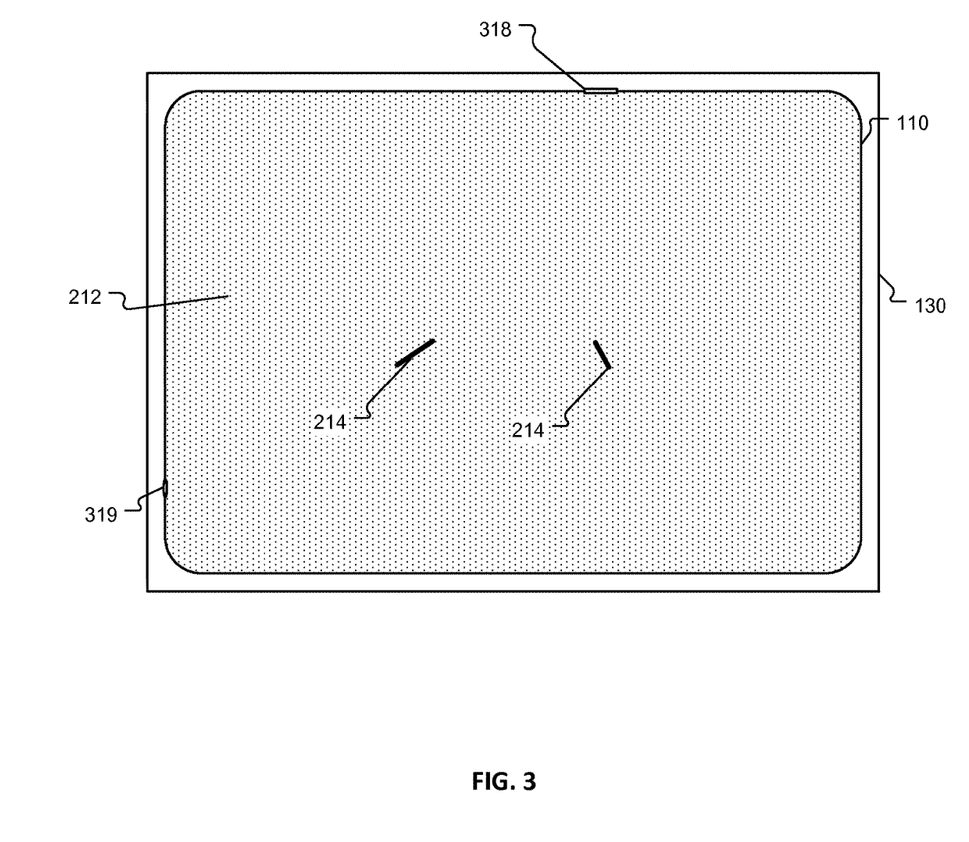
FIG. 3 illustrates an example image of an object, in accordance with embodiments of the present invention.

FIG. 3 illustrates an example image of an object 110, in accordance with embodiments of the present invention. As illustrated, an image of the cover glass 212 may have been captured by the imaging device 160, and the image may include the cracks 214, if any, of the cover glass 212. It is to be understood that although the cracks 214 are depicted darkly, under some embodiments the cover glass 212 may have a dark image and the cracks 214 may have a light image. This may be due to the reflected light 242 from the cover glass 212 that may generally not be captured by the imaging device 160 (e.g., under exposed), however the scattered light 244 from the crack 214 may generally be captured by the imaging device 160 (e.g., over exposed). It is to be understood that the embodiment is not limited to scattered light 244 from cracks 214, but may include scratches, chips and the like, including those located on the opposing surface of the cover glass 212 or located internally to the cover glass 212. In some embodiments, the image may capture visible portions of the support fixture 130. The image may also capture visible portions of components located on the side surfaces of the object 110, such as an electronic device's universal serial bus (USB) port 318, an audio jack 319, and the like.

Although not shown, the object 110 may be turned over and an image of the second surface of the object 110 opposed to the cover glass 212, or the first surface, may be captured. For example, the back cover of an electronic device may be captured in an embodiment. Furthermore, although not shown, an image of a graphical display or a display screen, such as a liquid crystal display (LCD), may be captured by the imaging device 160. Under this embodiment, the lighting assembly 140 may not be utilized to emit light to the LCD because the LCD may include backlighting that may emit sufficient light to capture and document defects of the LCD by the imaging device 160. For example, the LCD may have damage such as visible horizontal or vertical lines that may be documented by the imaging device 160.

Figure 4:
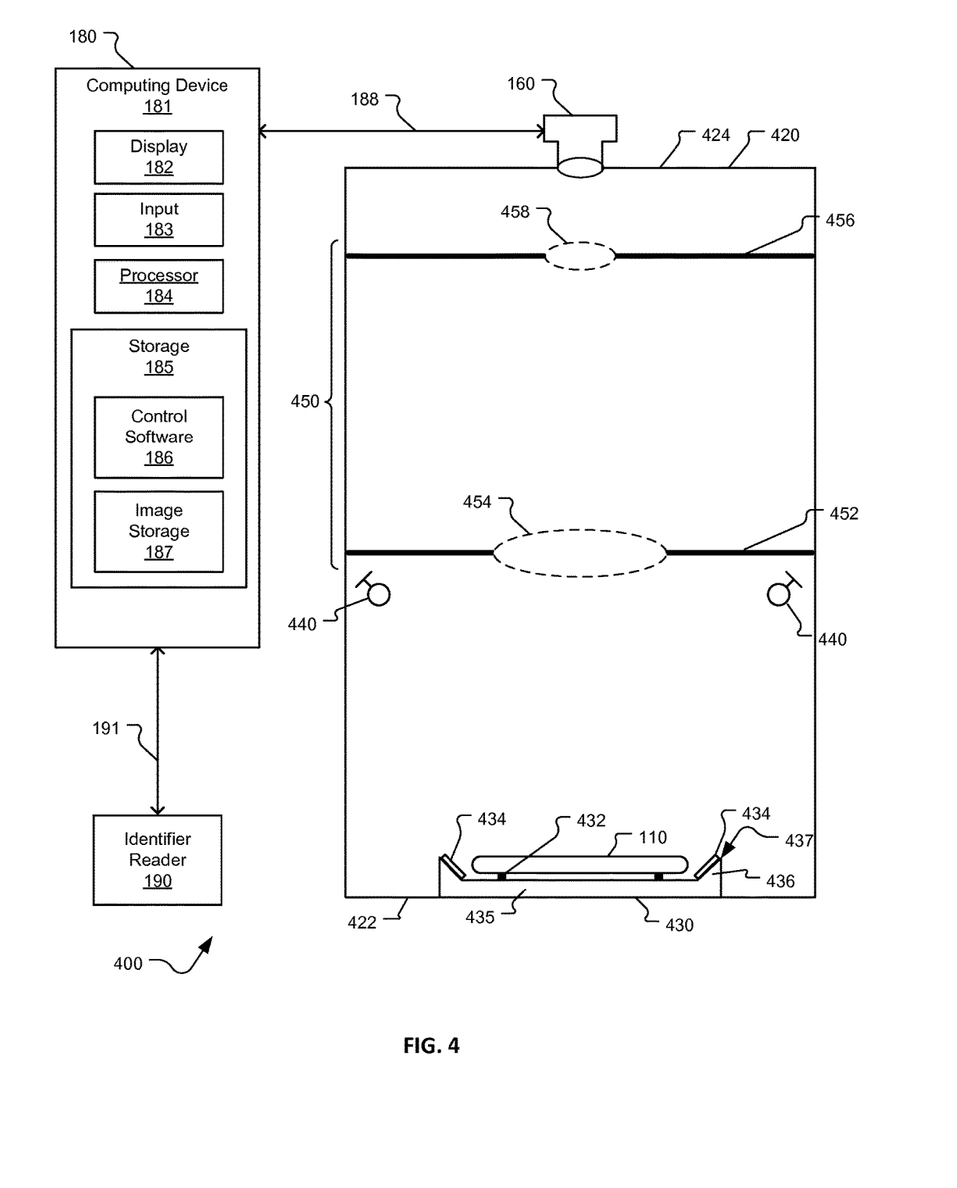
FIG. 4 is a block diagram illustrating an inspection system, in accordance with embodiments of the present invention.

FIG. 4 is a block diagram illustrating an inspection system 400, in accordance with embodiments of the present invention. Similar to FIG. 1, an embodiment of FIG. 4 shows that the object 110, such as an electronic device, may be placed at the first end 422 of the enclosure 420 and the imaging device 160 may be positioned at the second end 424 of the enclosure 420 that may capture an image of the object 110. As illustrated in FIG. 4, the support fixture 430 may be positioned at the first end 422 of the enclosure 420 and may comprise at least one mirror 434. Under some embodiments, the support fixture may comprise a base 435 and at least one wedge 436 positioned at the periphery or edge of the base 435. The wedge 436 may have a front surface 437 that is angled or tapered toward the base 435, such that when the mirror 434 is coupled to the wedge 436 at the front surface 437, the mirror is at an angle with respect to the object 110. In some embodiments, the wedge 436 may have a thicker end tapering to a thinner end of the wedge 436. Under some embodiments, the wedge 436 may be a platform, a shim, a spacer, a protrusion, or the like. Each respective mirror 434 may be affixed to the front surface 437 of the respective wedge 436. Each respective mirror 434 may be positioned at an angle relative to the object 110 to reflect a mirror image reflection of a side surface of the object 110 to the imaging device 160. In some embodiments, the support fixture 430 may include at least one support component 432, similar to support component 132. In an embodiment, the support component 432 may be a platform to lift the object 110 off of the surface of the support fixture 430. Such a support component 432 may allow for a reflected portion of the second surface opposed to the first surface of the object 110 to be partially visible via the mirror 434.

Under some embodiments, the mirror 434 may have one or more curvatures. For example, a mirror with a curved reflected surface may be used to enable the imaging of an object with a non-planar or three-dimensional geometry, such as a warped or uneven surface. A curvature may be convex, concave, or a combination of convex and concave. Such curvatures may provide wider fields of view, magnified views and any combination of such, with respect to the object 110 or portions of the object 110. Under some embodiments, a curvature may cause portions of a non-planar surface of the object 110 to appear planar with respect to an image captured by the imaging device 160.

Under some embodiments, the support fixture 430 may include one or more corrective optics or corrective lenses to adjust an image reflected by the mirror 434, for example a focal point may be adjusted such that the distance of the focal point with respect to the imaging device 160 may be lengthened or shortened, which may cause a higher magnification or a wider angle of view of the object 110. A corrective lens may be positioned between the mirror 434 and the object 110 or positioned between the mirror 434 and the imaging device 160. A corrective lens may improve the focus of the object 110 or portions of the object 110.

The enclosure 420 may include the lighting assembly 440 comprising one or more light sources, similar to the lighting assembly 140 of FIG. 1. As shown in FIG. 4, the lighting assembly 440 may be positioned so that the light source of the lighting assembly 440 is not reflected in the mirror 434 toward the imaging device 160. For example, the lighting assembly 140 may be positioned so that an image of the lighting assembly 440 may not be captured by the imaging device 160. Furthermore, the lighting assembly 440 may also be positioned to reduce over exposure of the object 110 caused by the mirror 434. Such positioning of the lighting assembly 440 may include the angle of incidence of each light source with respect to the normal of the first surface of the object 110. The angle of incidence may be greater than 0 degrees and less than 90 degrees. In some embodiments, as depicted in FIG. 4, the angle of incidence may be greater than 0 degrees and less than about 45 degrees, or may be greater than about 30 degrees and less than about 40 degrees. Under some embodiments, the lighting assembly 440 may emit generally diffused light, such as fluorescent or incandescent lighting, or collimated light.

The enclosure 420 may include the shutter assembly 450 that may comprise one or more shutters, similar to the shutter assembly 150 of FIG. 1. As shown in FIG. 4, the shutter assembly 450 may comprise the first shutter 452 having the first opening 454 and the second shutter 456 having the second opening 458. In some embodiments, as shown in FIG. 4, the first shutter 452 may be positioned between the lighting assembly 440 and the opposing second end 424 of the enclosure 420, and the second shutter 456 may be positioned between the first shutter 452 and the second end 424 of the enclosure 420. In some embodiments, the first shutter 452 may be positioned proximate the lighting assembly 440.

Figure 5:
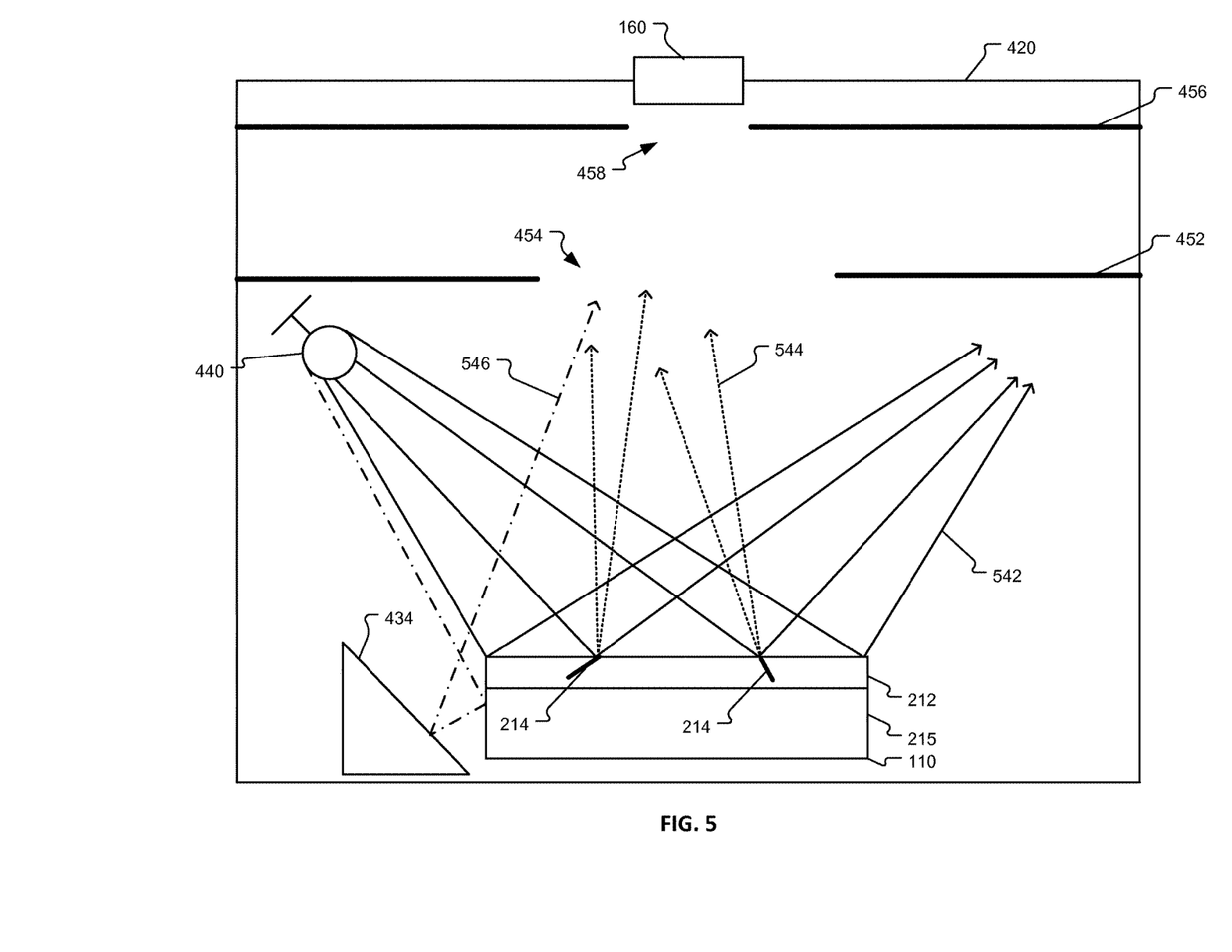
FIG. 5 is a block diagram illustrating a schematic cross-sectional view of an enclosure, in accordance with embodiments of the present invention.

FIG. 5 is a block diagram illustrating a schematic cross-sectional view of the enclosure 420, in accordance with embodiments of the present invention. Similar to FIG. 2, an embodiment of FIG. 5 shows that the lighting assembly 440 may emit light toward the object 110. As illustrated, light from the lighting assembly 440 may be emitted toward the cover glass 212 of the object 110, which may become reflected light 542 or scattered light 544. Reflected light 542 may be reflected by the cover glass 212 and may be partially blocked from passing past the first shutter 452 or the second shutter 456. Scattered light 544 may be scattered by the crack 214, and may pass through the first opening 454 of the first shutter 452 and through the second opening 458 of the second shutter 456 to the imaging device 160.

The lighting assembly 440 may comprise one or more light sources, which may emit generally, approximately, or substantially diffused light. For example, as illustrated in FIG. 5, light emitted from the light source of the lighting assembly 440 is illustrated with substantially diffused or generally non-parallel rays of light, which may be reflected or scattered. It is to be understood that collimated light may be utilized under some embodiments.

As shown in FIG. 5, one or more mirrors 434 may direct mirrored light 546 to the imaging device 160. For example, the imaging device 160 may receive a mirror like reflection or a specular reflection from the mirror 434. The mirror 434 may be positioned or angled to direct the mirror image of the side surface of the object 110 to the imaging device 160 via mirrored light 546. In some embodiments, the mirror may be a front coated mirror, a front surface mirror, a first surface mirror, or the like. A mirror in which a reflective coating is applied on a surface of a substrate may maximize the amount of light reflected, may minimize distortion of an image, and may reduce the ghosting effect compared to a standard mirror in which a reflective coating is applied behind a transparent substrate.

Figure 6:
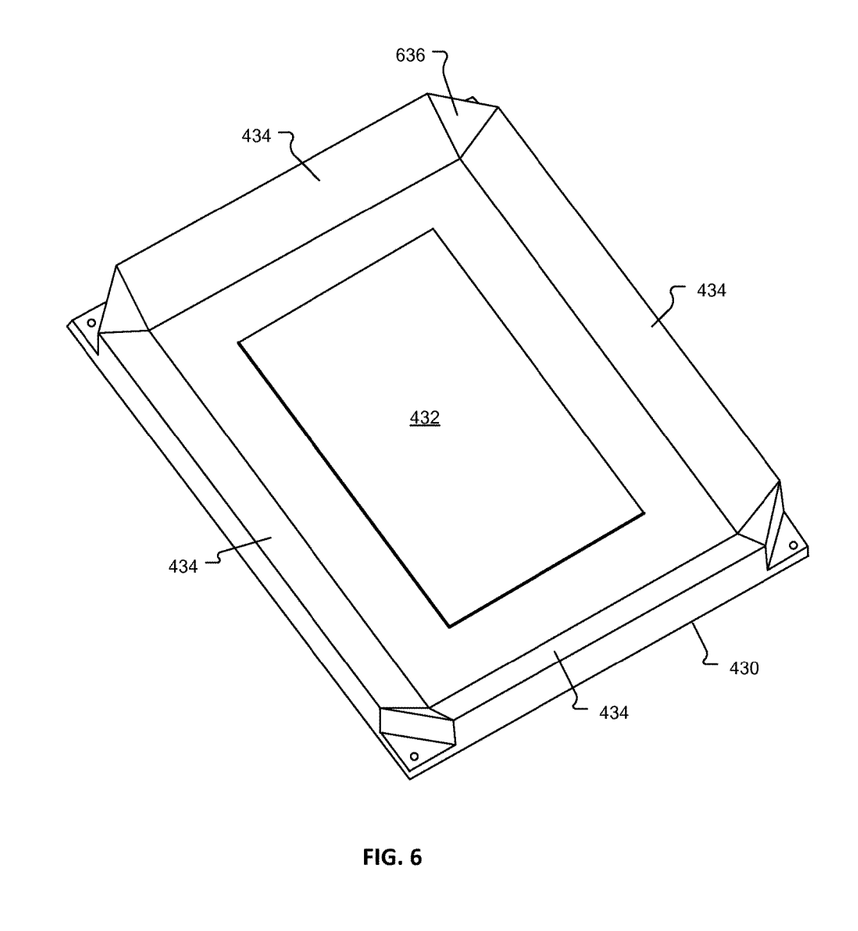
FIG. 6 illustrates an example perspective view of a support fixture, in accordance with embodiments of the present invention.

FIG. 6 illustrates an example perspective view of a support fixture 430, in accordance with embodiments of the present invention. The support fixture 430 may include the support component 432 and four mirrors 434 to respectively reflect to the imaging device 160 an image of one of four side surfaces of the object 110, such as an electronic device. Each mirror may be coupled to the support fixture 430, such as with an adhesive. Under some embodiments, each mirror may be sized to facilitate capture of an image of a reflection of the side or edge of the object 110. Under an embodiment, a mirror may be positioned at the corner 636 of the fixture 430 to facilitate capture of an image of a reflection of a corner of the object 110.

Figure 7:
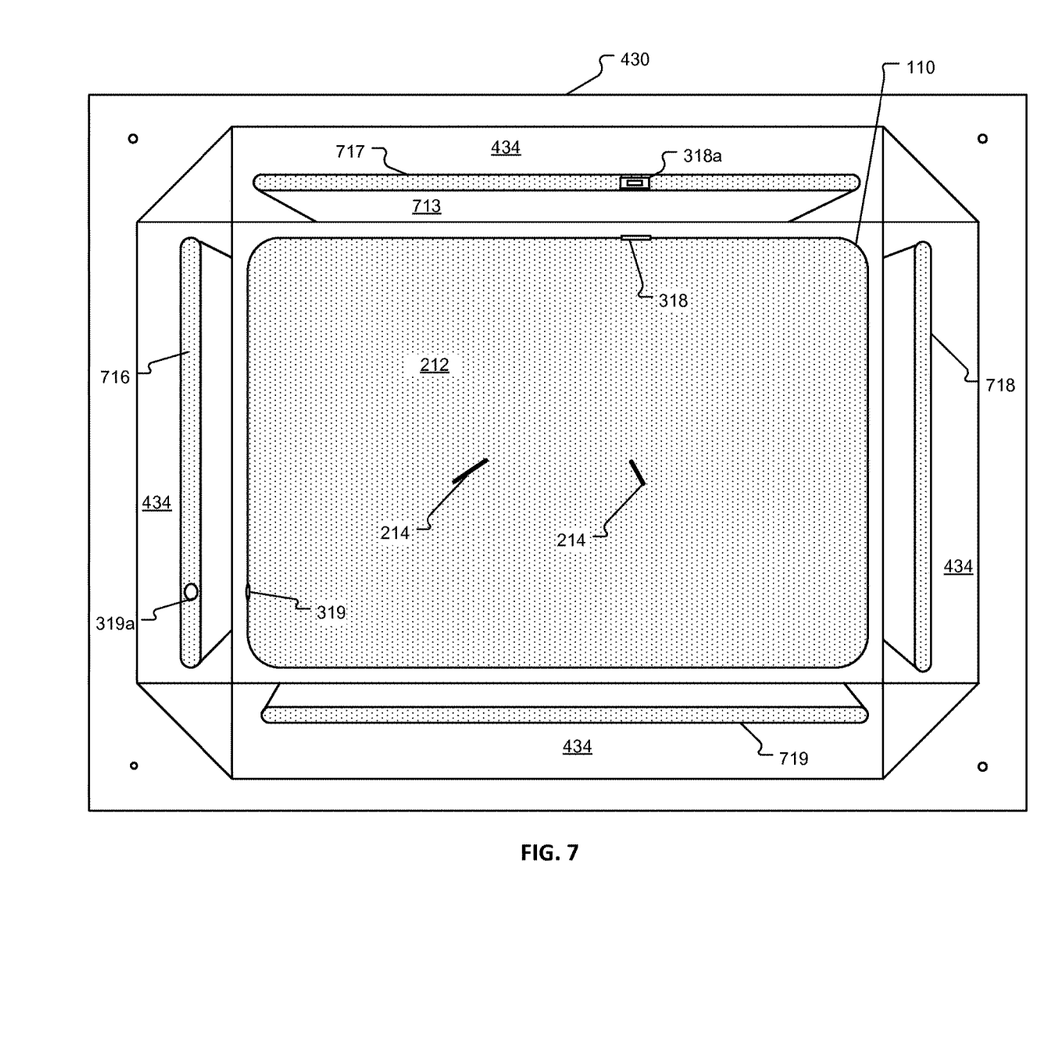
FIG. 7 illustrates an example image of an object, in accordance with embodiments of the present invention.

FIG. 7 illustrates an example image of the object 110, in accordance with embodiments of the present invention. As illustrated, an image of the cover glass 212 may have been captured by the imaging device 160, and the image may include the cracks 214, if any, of the cover glass 212. In some embodiments, similar to FIG. 3, the image may capture visible portions of components located on the side surfaces of the object 110, such as an electronic device's universal serial bus (USB) port 318, an audio jack 319, and the like.

In addition, because of the four mirrors 434, the image may include a first side surface 716, a second side surface 717, a third side surface 718, and a fourth side surface 719 of the object 110. Furthermore, components or damage of the side surface may be visible in the mirrored images. For example, the image of the second side surface 717 may include a mirror image of the USB port 318a, and the image of the first side surface 716 may include a mirror image of the audio jack 319a. It is to be understood that the mirror image of the side surface may document damage or defects of an electronic device such as bezel damage, housing damage, port damage, rear cover pop out or separation, and the like. In addition, portions of the second surface 713 of the object 110 may be included in the mirror image, which may document additional damage to the second surface. Although not shown, the object 110 may be turned over and an image of the second surface 713 opposed to the cover glass 212 may be captured. For example the back cover and the corresponding side surfaces of an electronic device may be captured in an embodiment. In some embodiments, the general external condition of the object 110 may be documented, for example, the image as depicted in FIG. 7 may document the general "wear and tear" condition of the object 110 with respect to the cover glass 212, the side surfaces 716, 717, 718, 719, and portions of the second surface 713. It is to be understood that the side surfaces 716, 717, 718, 719 of the object 110 are between the first surface or cover glass 212 and the second surface 713.

Figure 8:
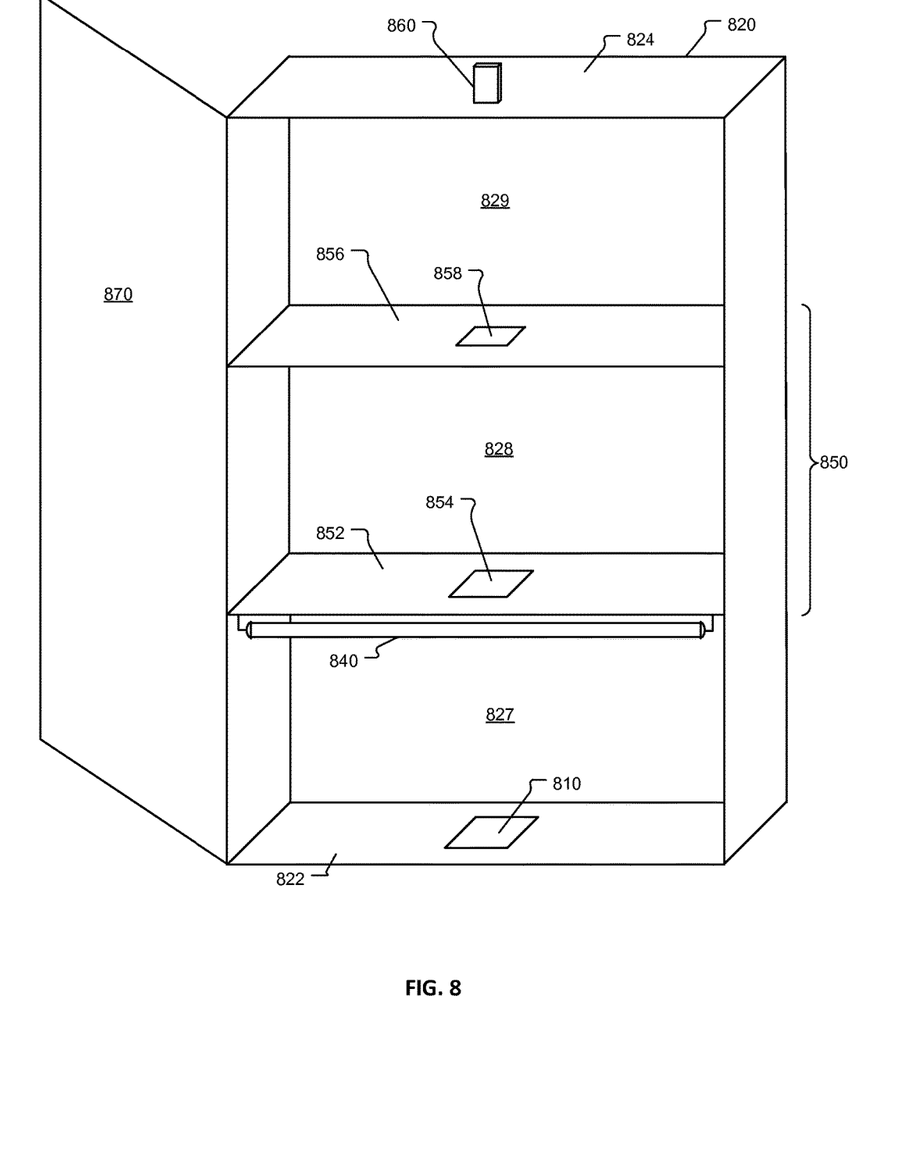
FIG. 8 illustrates an example perspective schematic view of an enclosure, in accordance with embodiments of the present invention.

FIG. 8 illustrates an example perspective schematic view of an enclosure 820, in accordance with embodiments of the present invention. As illustrated, the enclosure 820 may include the object 810 at the first end 822 of the enclosure 820, and the imaging device 860 at the second end 824 of the enclosure 820. The enclosure 820 may include the lighting assembly 840 comprising one or more light sources. The enclosure 820 may also include the shutter assembly 850 comprising the first shutter 852 that includes the first opening 854 and the second shutter 856 that includes the second opening 858. As discussed above, the lighting assembly 840 may be proximate the object 810 such as for side lighting, or may be positioned at a distance from the object 810 such as for diffused lighting. The first shutter 852 may be proximate the lighting assembly 840, and may be positioned between the lighting assembly 840 and the second end 824 of the enclosure, and the second shutter 856 may be positioned between the first shutter 852 and the second end 824 of the enclosure. In some embodiments, the second shutter 856 may be positioned proximate the second end 824, or proximate the imaging device 860. In alternative embodiments, the second shutter 856 may be positioned approximately halfway between the distance from the first shutter 852 and the second end 824 of the enclosure 820. The enclosure 820 may have the access component 870, such as a door, to allow the object 810 to be placed in the enclosure 820, after which the access component 870 may be sealed or closed to prevent or reduce exterior light from entering the enclosure 820. As illustrated in FIG. 8, the enclosure 820 may comprise the first portion 827, the second portion 828 separated from the first portion 827 by the first shutter 852, and the third portion 829 separated from the second portion 828 by the second shutter 856.

Figure 9:
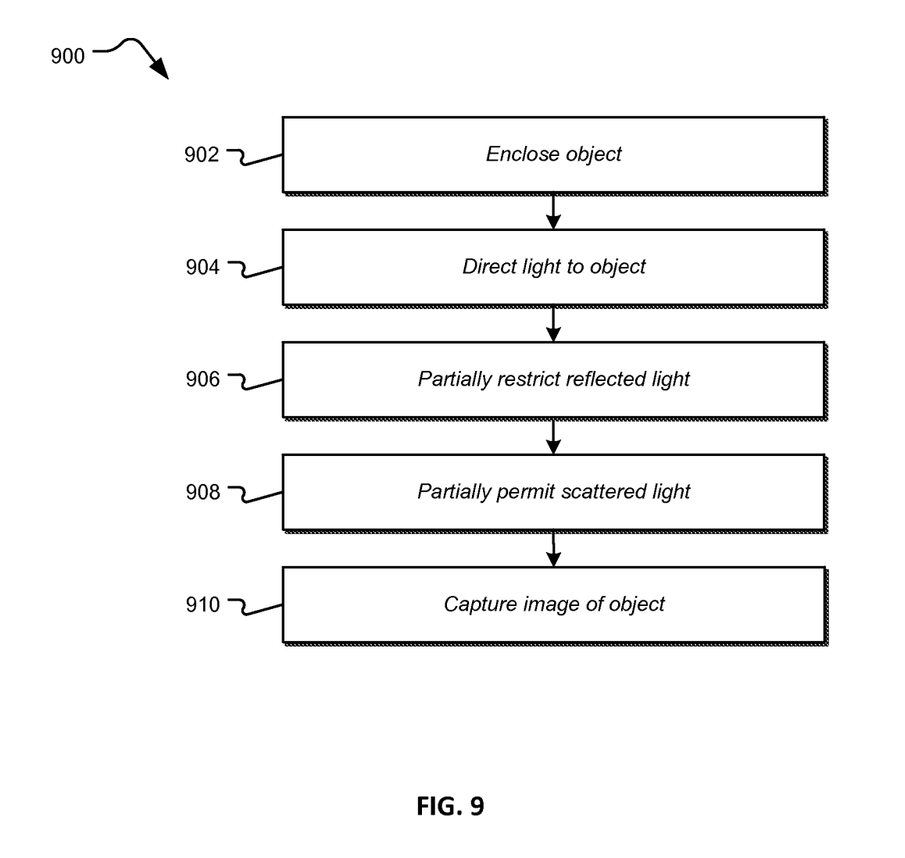
FIG. 9 illustrates an example flow diagram of a process of capturing an image of an object, in accordance with various embodiments of the present invention.

FIG. 9 illustrates an example flow diagram of a process 900 of capturing an image of the object 810, in accordance with various embodiments of the present invention. At step 902, the object 810 may be enclosed by the enclosure 820 and the object 810 may be positioned at the first portion 827 of the enclosure 820. Under some embodiments, the object 810 may be cleaned before placing the object 810 in the enclosure 820, in order to remove dirt, fingerprints, and the like. Such may prevent or reduce interference of the capture of an image of damage or defects of the object 810.

At step 904, light from one or more light sources of the lighting assembly 840 may be emitted toward the object 810. As discussed above, the lighting assembly 840 may be positioned proximate the object 810 or may be positioned at a distance from the object 810. The light from the lighting assembly 840 may be collimated or diffused.

At step 906, reflected light that is reflected from the object 810 may be partially restricted by the first shutter 852 from reflecting from the first portion 827 to the second portion 828 of the enclosure 820, in which the first portion 827 and the second portion 828 of the enclosure 820 is separated by the first shutter 852. In addition, the reflected light may be partially restricted by the second shutter 856 from reflecting from the second portion 828 to the third portion 829 of the enclosure 820, in which the second portion 828 and the third portion 829 of the enclosure 820 are separated by the second shutter 856.

At step 908, scattered light that is scattered from the object 810 may be partially allowed by the opening 854 of the first shutter 852 to scatter from the first portion 827 to the second portion 828 of the enclosure 820. In addition, scattered light may be partially allowed by the second opening 858 of the second shutter 856 to scatter from the second portion 828 to the third portion 829 of the enclosure 820, and be received by the imaging device 860. Under some embodiments, mirrored light that may be reflected from the mirror 434 may be partially allowed by the first opening 854 and the second opening 858 to be reflected to the imaging device 860. Such mirrored light may reflect light reflected from the side surface of the object 810.

At step 910, an image of the object 810 may be captured with the imaging device 860 coupled to the third portion 829 of the enclosure 820 opposite the object 810. In some embodiments, the imaging device 860 may be controlled by the control system 180.

Embodiments of the present invention may provide various advantages not provided by prior art systems. An exemplary advantage of some disclosed embodiments may be that an image of a cover glass or cover sheet may be captured while it is attached to an opaque object, device, substrate, or component, such as a housing of an electronic device. For example, an image of a cover glass may be captured without removing the cover glass from the housing, and that image may capture a defect, such as a thin crack or fracture, that is imperceptible under certain lighting conditions, such as with a ceiling lamp. Another exemplary advantage of some disclosed embodiments may be the reduction of cost in equipment and materials. For example, an off-the-shelf camera may be utilized to capture an image of a cover glass with reduced undesirable reflection of an operator holding the camera, or with reduced undesirable reflection of objects behind the camera, such as a wall or ceiling. For further example, the automatic focus functionality of a camera may be better utilized for focusing on the object, with a reduced tendency of focusing on objects surrounding a device, such as an operator's hand supporting the object. Another exemplary advantage of some disclosed embodiments may be that more consistent lighting conditions of an object may be achieved, which may enhance the contrast, resolution, exposure, and the like of an image of the object. Another exemplary advantage of some disclosed embodiments may be the storage or tracking of images taken of objects. For example, a captured image may be associated with an object identifier, such as a data source name, which may facilitate enhanced communication across different entities with respect to the captured image.

While the invention has been described in terms of particular embodiments and illustrative figures, those of ordinary skill in the art will recognize that the invention is not limited to the embodiments or figures described. Many of the embodiments described above in relation to a cover glass may be applied to other embodiments of transparent and protective cover sheets through which a graphical display or a display screen is viewed. For example, a cover sheet may be comprised of a glass substitute comprising a plastic material. Furthermore, many of the embodiments described above may be applied to a cover glass or a cover sheet that is semi-transparent or opaque. Additionally, many of the embodiments of the invention described above in relation to an electronic device may be applied to any device, object or equipment that comprises an external glass or transparent surface, for example solar panels, framed pictures, automotive glass, and the like.

Although various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those of ordinary skill in the art and, consequently, are not described in detail herein. If embodied in software, each block or step may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical function(s).

Although the processes, flowcharts and methods described herein may describe a specific order of execution, it is understood that the order of execution may differ from that which is described. For example, the order of execution of two or more blocks or steps may be scrambled relative to the order described. Also, two or more blocks or steps may be executed concurrently or with partial concurrence. Further, in some embodiments, one or more of the blocks or steps may be skipped or omitted. It is understood that all such variations are within the scope of the present disclosure.

Also, any logic or application described herein that comprises software or code can be embodied in any non-transitory computer-readable medium for use by or in connection with an instruction execution system such as a processing component in a computer system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable media include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A system for inspecting an electronic device having a cover glass, the system comprising:
    an enclosure comprising a first end, a second end opposing the first end, and four walls between the first end and the second end;
    a support fixture positioned in the enclosure at the first end and configured to support the electronic device;
    a lighting assembly comprising one or more light sources configured to emit light toward the cover glass, wherein the lighting assembly is positioned between the support fixture and the second end;
    a shutter assembly comprising:
        a first shutter comprising a first opening, wherein the first shutter is positioned between the lighting assembly and the second end; and
        a second shutter comprising a second opening, wherein the second shutter is positioned between the first shutter and the second end;
    a camera positioned at the second end and configured to receive light reflected from the cover glass and generate image data indicative of a visible flaw of the cover glass; and
    a control system communicatively coupled to the camera, wherein the control system is programmed to store the image data with an identifier corresponding to the electronic device being inspected.

2. The system of claim 1, wherein:
    each of the one or more light sources is configured to emit light toward the cover glass at a grazing angle of incidence with respect to the cover glass.

3. The system of claim 1, wherein:
    the support fixture comprises a base, a wedge coupled to a periphery of the base and having a front surface angled with respect to the base, and a mirror coupled to the front surface of the wedge and positioned to reflect light reflected from a side surface of the electronic device; and
    the camera is further positioned to receive the light reflected by the mirror.

4. A system for inspecting an object having an opaque component and a cover glass coupled to the opaque component, the system comprising:
    an enclosure comprising a first end, a second end opposing the first end, and four walls between the first end and the second end;
    a support fixture positioned in the enclosure at the first end and configured to support the object;
    a lighting assembly positioned between the support fixture and the second end, wherein the lighting assembly comprises one or more light sources configured to emit light toward the cover glass;
    an imaging device positioned at the second end and configured to receive reflected light from the object and generate corresponding image data; and
    a shutter assembly positioned between the lighting assembly and the imaging device, wherein the shutter assembly is configured to allow the reflected light to be received by the imaging device, wherein the reflected light is indicative of a visible flaw of the object.

5. The system of claim 4, wherein:
    each of the one or more light sources is configured to emit light toward the cover glass at a grazing angle of incidence with respect to the cover glass.

6. The system of claim 4, wherein:
    the shutter assembly comprises:
        a first shutter comprising a first opening, wherein the first shutter is positioned between the lighting assembly and the imaging device and is positioned proximate the lighting assembly, wherein the first shutter allows the reflected light to pass through the first opening; and
        a second shutter comprising a second opening, wherein the second shutter is positioned between the first shutter and the imaging device, wherein the second shutter allows the reflected light to pass through the second opening.

7. The system of claim 6, wherein:
    the shutter assembly further comprises a third shutter comprising a third opening, wherein the third shutter is positioned between the second shutter and the imaging device, wherein the third shutter allows the reflected light to pass through the third opening.

8. The system of claim 4, wherein:
    the lighting assembly comprises four groups, wherein each group comprises a plurality of light sources, wherein each of the four groups is respectively coupled to a respective one of the four walls of the enclosure, wherein the four groups surround the support fixture.

9. The system of claim 4, wherein:
    each of the one or more light sources is further configured to emit light toward a side surface of the opaque component; and
    the support fixture further comprises a support component configured to elevate the object and a mirror positioned to reflect light from the side surface of the opaque component.

10. The system of claim 9, wherein:
the support fixture comprises a corrective lens located between the mirror and the object, wherein the corrective lens adjusts the light reflected by the object to lengthen a distance of a focal point with respect to the imaging device.

11. The system of claim 4, further comprising:
a reader configured to determine an identifier of the object; and
a control system communicatively coupled to the imaging device and the reader, wherein the control system is programmed to store the image data with the identifier.

12. The system of claim 4, wherein:
the imaging device is a camera comprising a lens and a polarizing filter coupled to the lens.

13. A method of inspecting a device, the method comprising:
directing light, from a lighting assembly comprising one or more light sources, to a front surface of the device positioned within an enclosure, wherein at least a portion of the light is directed toward the front surface of the device at a first angle of incidence with respect to the front surface of the device;
directing light from the lighting assembly to a side surface of the device;
receiving, at a camera configured to receive light reflected from the device, light reflected from the front surface;
receiving, at the camera, reflected light reflected from a mirror positioned to reflect light reflected from the side surface;
generating, by the camera, image data based on the reflected light, wherein said generating, by the camera, the image data is further based on the reflected light reflected from the mirror; and
determining at least one visible flaw of the device based on the image data.

14. The method of claim 13, further comprising:
adjusting light reflected from the side surface, wherein a distance of a focal point of the light is lengthened, wherein the side surface is a non-planar surface.

15. The method of claim 13, wherein:
said directing light, from the lighting assembly comprising one or more light sources, to the front surface of the device further comprises directing the light to the front surface at a grazing angle of incidence with respect to the front surface.

16. The method of claim 13, further comprising:
determining an identifier of the device; and
storing the image data with the identifier.

17. The method of claim 13, further comprising:
filtering polarized light reflected from an interior surface of the enclosure to generate filtered light, wherein the light reflected from the interior surface of the enclosure is received from the light reflected from the front surface of the device; and
receiving, at the camera, the filtered light.

18. The method of claim 13, further comprising:
allowing, by a shutter assembly, the reflected light to be received by the camera.

19. The method of claim 13, further comprising:
said directing light, from the lighting assembly comprising one or more light sources, to the front surface of the device further comprises directing surrounding light to the front surface.

* * * * *